United States Patent
Wang et al.

(10) Patent No.: US 9,164,108 B2
(45) Date of Patent: Oct. 20, 2015

(54) LIPOSOME-BASED MICROARRAY AND METHODS OF USE THEREOF

(75) Inventors: Denong Wang, Palo Alto, CA (US); Leonore A. Herzenberg, Stanford, CA (US); Lawrenes Steinman, Stanford, CA (US)

(73) Assignee: SRI INTERNATIONAL, Menlo Park, CA (US)

( * ) Notice: Subject to any disclaimer, the term of this patent is extended or adjusted under 35 U.S.C. 154(b) by 1859 days.

(21) Appl. No.: 11/387,993

(22) Filed: Mar. 22, 2006

(65) Prior Publication Data

US 2007/0059765 A1    Mar. 15, 2007

Related U.S. Application Data

(60) Provisional application No. 60/664,251, filed on Mar. 22, 2005.

(51) Int. Cl.
| | | |
|---|---|---|
| *G01N 33/543* | (2006.01) | |
| *G01N 33/577* | (2006.01) | |
| *G01N 33/92* | (2006.01) | |
| *B01J 19/00* | (2006.01) | |

(52) U.S. Cl.
CPC ............ *G01N 33/92* (2013.01); *B01J 19/0046* (2013.01); *G01N 33/5432* (2013.01); *G01N 33/54386* (2013.01); *G01N 33/577* (2013.01); *B01J 2219/0065* (2013.01); *B01J 2219/0074* (2013.01); *B01J 2219/00527* (2013.01); *B01J 2219/00603* (2013.01); *B01J 2219/00639* (2013.01); *B01J 2219/00659* (2013.01); *B01J 2219/00734* (2013.01); *G01N 2800/26* (2013.01)

(58) Field of Classification Search
CPC .. G01N 33/5432; G01N 33/577; G01N 33/92
See application file for complete search history.

(56) References Cited

U.S. PATENT DOCUMENTS

| | | | |
|---|---|---|---|
| 6,433,148 B1* | 8/2002 | Abrahan et al. | 530/388.1 |
| 2003/0096418 A1* | 5/2003 | Yamazaki et al. | 436/43 |
| 2004/0002064 A1 | 1/2004 | Fang et al. | |
| 2004/0033624 A1 | 2/2004 | Zweig | |
| 2004/0137475 A1* | 7/2004 | Haugland et al. | 435/6 |
| 2004/0241765 A1* | 12/2004 | Zweig | 435/7.2 |
| 2004/0259142 A1* | 12/2004 | Chai et al. | 435/6 |
| 2005/0032246 A1* | 2/2005 | Brennan et al. | 436/518 |

(Continued)

FOREIGN PATENT DOCUMENTS

WO    WO 2006/102687    9/2006

OTHER PUBLICATIONS

Binder, C.J. et al. (2003) "Pneumococcal Vaccination Decreases Atherosclerotic Lesion Formation: Molecular Mimicry Between *Streptococcus pneumoniae* and Oxidized LDL," Nat. Med. 9: 736-743.

(Continued)

*Primary Examiner* — Bao Thuy L Nguyen
*Assistant Examiner* — Gary E Hollinden
(74) *Attorney, Agent, or Firm* — Richard Aron Osman

(57) ABSTRACT

This invention provides novel liposome-based articles of manufacture and microarrays and methods of making and using them (1) to detect the presence of one or more agents in a sample, (2) to determine the amount of one or more agents in a sample, and (3) to determine whether a subject is afflicted with a disorder. This invention also provides kits which comprise the instant microarrays.

24 Claims, 4 Drawing Sheets

(56) References Cited

U.S. PATENT DOCUMENTS

2005/0182242 A1* 8/2005 Snyder et al. .................. 530/350
2007/0116733 A1* 5/2007 Graneli et al. ................. 424/423

OTHER PUBLICATIONS

Chang, M.K. et al. (2004) "Apoptotic Cells With Oxidation-Specific Epitopes Are Immunogenic and Proinflammatory," *J. Exp. Med.* 200: 1359-1370.

Fukui, S. et al. (2002) "Oligosaccharide Microarrays for High-throughput Detection and Specificity Assignments of Carbohydrate-protein Interactions," *Nat. Biotechnol.* 20: 1011-1017.

Hava, D.L. et al. (2005) "CD1 Assembly and the Formation of CD1-antigen Complexes," *Curr. Opin. Immunol.* 17: 88-94.

Hörkkö, S. et al. (2000) "Immunological Responses to Oxidized LDL," *Free Radic. Biol. Med.* 28: 1771-1779.

Howe, C.L. et al. (2004) "Antiapoptotic Signaling by a Remyelination-promoting Human Antimyelin Antibody," *Neurobiol. Dis.* 15: 120-131.

Merrill, J.E. (1992) "Autoimmune Disease and the Nervous System-Biochemical, Molecular, and Clinical Update," *West J. Med.* 156: 639-646.

Misasi, R. et al. (1997) "Gangliosides and Autoimmune Diabetes," *Diabetes/Metab. Rev.* 13: 163-179.

Moran, A.P. et al. (2001) "Molecular Mimicry in *Campylobacter jejuni* and *Helicobacter pylori* Lipopolysaccharides: Contribution of Gastrointestinal Infections to Autoimmunity," *J. Autoimmun.* 16: 241-256.

Moran, A.P. et al. (1996) "Molecular Mimicry of Host Structures by Bacterial Lipopolysaccharides and its Contribution to Disease," *FEMS Immunol. Med. Microbiol.* 16:105-115.

Nojima, J. et al. (2004) "Strong Correlation Between the Prevalence of Cerebral Infarction and the Presence of Anti-cardiolipin/β2-glycoprotein I and Anti-Phosphatidylserine/prothrombin Antibodies—Co-existence of These Antibodies Enhances ADP-induced Platelet Activation in Vitro," *Thromb. Haemost.* 91: 967-976.

Pedotti, R. et al. (2003) "Multiple Elements of the Allergic Arm of the Immune Response Modulate Autoimmune Demyelination," *Proc. Natl. Acad. Sci. U.S.A.* 100: 1867-1872.

Pedotti, R. et al. (2003) "Severe Anaphylactic Reactions to Glutamic Acid Decarboxylase (GAD) Self Peptides in NOD Mice that Spontaneously Develop Autoimmune Type 1 Diabetes Mellitus," *BMC Immunol.* 4: 2 (pp. 1-9).

Robinson, W.H. et al. (2003) "Protein Microarrays Guide Tolerizing DNA Vaccine Treatment of Autoimmune Encephalomyelitis," *Nat. Biotechnol.* 21: 1033-1039.

Shaw, P.X. et al. (2003) "The Autoreactivity of Anti-phosphorylcholine Antibodies for Atherosclerosis-Associated Neoantigens and Apoptotic Cells," *J. Immunol.* 170: 6151-6157.

Singh, A.K. et al. (2001) "Natural Killer T Cell Activation Protects Mice Against Experimental Autoimmune Encephalomyelitis," *J. Exp. Med.* 194: 1801-1811.

Van Kaer, L. (2004) "Regulation of Immune Responses by CD1d-restricted Natural Killer T Cells," *Immunol. Res.* 30: 139-153.

Wang, D. (2003) "Carbohydrate Microarrays," *Proteomics* 3: 2167-2175.

Wang, D. et al. (2002) "Carbohydrate Microarrays for the Recognition of Cross-reactive Molecular Markers of Microbes and Host Cells," *Nat. Biotechnol.* 20: 275-281.

Wang, D. et al. (2004) "Glycan Arrays Lead to the Discovery of Autoimmunogenic Activity of SARS-CoV," *Physiol. Genomics* 18: 245-248.

PCT International Preliminary Report on Patentability issued Sep. 25, 2007 for International Application Publication No. WO 2006/102687 published Sep. 28, 2006.

* cited by examiner

Images of stained "mini" arrays

Figure 3B

| 2 | | 1 | 3 | 5 |
|---|---|---|---|---|
| 3 | A | *Dex2000K-FITC 0.1mg/ml* | ST-IM5-ptc 11.6 mg/2mg/ml DW757 | FITC-ptc 1:5dil of the AK Prep |
| 4 | B | 1:3 in saline | 1:3 in saline | 1:3 in saline |
| 5 | C | 1:9 in saline | 1:9 in saline | 1:9 in saline |
| 6 | D | 1:27 in saline | 1:27 in saline | 1:27 in saline |
| 7 | E | Saline-ptc 2mg/ml Prep73104 | *ST-Dex-ptc 0.1mg/2mg/ml Prep73104* | NGL201 0.04mg/2mg/ml DW754 |
| 8 | F | 1:3 in saline | *1:3 in saline* | 1:3 in saline |
| 9 | G | 1:9 in saline | *1:9 in saline* | 1:9 in saline |
| 10 | H | 1:27 in saline | *1:27 in saline* | 1:27 in saline |
| 11 | | 2 | 4 | 6 |
| 12 | A | ST-IM3-ptc 0.1mg/2mg/ml Prep73104 | GM1-ptc 0.02 mg/2mg/ml DW762 | NGL203-ptc 0.04 mg/2mg/ml DW753 |
| 13 | B | 1:3 in saline | 1:3 in saline | 1:3 in saline |
| 14 | C | 1:9 in saline | 1:9 in saline | 1:9 in saline |
| 15 | D | 1:27 in saline | 1:27 in saline | 1:27 in saline |
| 16 | E | ST-IM4-ptc 4.6 mg/2mg/ml DW757 Prep72404 | GM1-ptc 0.2 mg/2mg/ml Prep52704 | NGL334-ptc 0.04 mg/2mg/ml DW755 |
| 17 | F | 1:3 in saline | 1:3 in saline | 1:3 in saline |
| 18 | G | 1:9 in saline | 1:9 in saline | 1:9 in saline |
| 19 | H | 1:27 in saline | 1:27 in saline | *Cy3, Cy5, FITC* |

LIPOSOME-BASED MICROARRAY AND METHODS OF USE THEREOF

This application claims the benefit of U.S. Provisional application No. 60/664,251, filed Mar. 22, 2005, the contents of which are hereby incorporated herein by reference.

BACKGROUND OF THE INVENTION

Like proteins and carbohydrates, lipids are a category of essential elements of living cells. Lipids play multiple physiological roles in all types of cells in a wide range of living species. In addition to their basic functions in energy metabolism/storage and formation of membranes and sub-cellular components, lipid molecules are important for cell-cell communication, cell signaling and intracellular signal transduction.

Lipid molecules of diverse structures are also an important target for immunologic recognition, such as the specific host recognition of microorganisms that are mediated by microbe-specific lipid or lipid-containing molecules. A major histocompatibility (MHC)-like protein, CD1, binds certain types of lipid molecules and presents them to T cells or NK cells [1, 2]. This unique antigen presentation system presents lipid antigens to effector T cells, which have diverse roles in anti-microbial responses, anti-tumor immunity and the regulation of the balance between tolerance and autoimmunity. Many bacterial pathogens produce phospholipids, glycolipids and/or lipopolysaccharides of distinct antigenic structures. Some are specific for given pathogen and thereby serve as biomarkers for pathogen identification and diagnosis of infectious diseases, and as vaccine targets for the induction of anti-infection immune responses.

Lipid moieties of cellular components may also be molecular targets of autoimmune diseases [3, 4]. In multiple sclerosis (MS) and autoimmune encephalomyelitis (EAE), there are increased T cell and autoantibody reactivities that are directed at myelin lipids [3-5]. These autoimmune responses are responsible for demyelination in central and/or peripheral neural tissues. In systemic lupus erythematosus (SLE), anti-cardiolipin antibodies were detected in addition to the autoantibodies to protein and nucleic acid components that were previously recognized [6]. CD1 expression is increased at the site of brain lesions in both MS and its rodent model, experimental autoimmune encephalomyelitis (EAE) [7-9].

Lipid-based antigenic cross-reactivities or molecular mimicry between cellular components and specific microbial antigens may contribute to either pathogenesis of infectious diseases or clearance of cellular lipid products [10-12]. *Campylobacter jejuni* infection induced an autoimmune neurological disorder Guillain-barre syndrome in a considerable proportion (~⅓) of cases [3, 4, 13]. This pathogen expresses a lipopolysaccharide molecule that mimics various gangliosides present in high concentrations in peripheral nerves. Infection by this bacterium may, thus, elicit undesired autoimmune responses to gangliosides of the host tissue. In addition, numerous viral infections induce this syndrome, since viruses collect gangliosides as they incorporate plasma membrane from the host cell. Therefore, precaution must be taken when we consider the use of the whole-viral preparations that are made by human or primate cells as vaccine candidates. Such vaccines may display the host-tissue derived lipid and glycolipid structures with altered antigenic reactivity and thus elicit undesired autoimmune responses.

Self-lipid components may be modified to generate neo-immunogenic lipid epitopes [14, 15]. For example, oxidation of low-density lipoprotein (LDL) generates a variety of oxidatively modified lipids and lipid-protein adducts that are immunogenic and proinflammatory, which in turn contribute to atherogenesis. Cells undergoing apoptosis also display oxidized moieties on their surface membranes, as determined by binding of oxidation-specific monoclonal antibodies. However, lipid-elicited autoantibodies are not always harmful. Some anti-lipid autoantibodies play roles in the clearance of non-essential or harmful cellular lipid derivatives and are, in fact, beneficial to the hosts [11, 15, 16]. In such circumstance, a microbial antigen may share structural similarity with the moieties of the latter category of cellular lipid derivatives and elicits the "beneficial autoantibodies" to bind and remove the "junk lipids" from the circulation. For example, there is molecular mimicry between *Streptococcus pneumoniae* and oxidized low-density lipoprotein (oxLDL) [15]. Immunization with cell-wall polysaccharide of *Streptococcus pneumoniae* elicited T15 anti-phosphorylcholine antibodies that cross-react with oxidized epitopes of low-density lipoprotein (oxLDL). The elevated LDL level is positively correlated to the progression of atherosclerosis and oxLDL has been identified in atherosclerotic lesions. Pneumococcal vaccination induced high circulating levels of oxLDL-specific IgM and decreased the extent of atherosclerosis in animal models [15].

Howe et al [16] reported that a human monoclonal IgM antibody directed against myelin induces antiapoptotic signaling in premyelinating oligodendrocytes and reduces caspase-3 activation and caspase gene expression in mice undergoing antibody-induced remyelination. Such autoantibody-mediated signaling may have important therapeutic implications for a variety of neurological diseases, including stroke and Alzheimer's disease.

In summary, lipids represent an important class of antigenic structures and have unique physiochemical properties. In view of their antigenic reactivities, there are two major categories of lipids: microbe-specific structures and host-tissue cross-reactive moieties. The former are able to induce pathogen-specific immune responses and are considered as candidate molecules for developing vaccines or diagnostic tool to combat infectious diseases. The latter may play roles in regulating the biological relationship of microbes and their hosts and in certain circumstances the induction of autoimmune responses. Some anti-self-lipid activities are, however, beneficial to the hosts. The outcome of an anti-lipid antibody response depends on multiple factors, including epitope-binding specificity of anti-lipid antibodies, tissue and subcellular distribution of lipid molecules, and the physiological and pathophysiological properties of the targeted lipid molecules.

SUMMARY OF THE INVENTION

This invention provides two articles of manufacture and four microarrays.

This invention also provides a method for detecting in a sample the presence of one or more agents which specifically bind to one or more known lipids, which method comprises: (a) contacting the sample with the above microarrays, wherein each known lipid is affixed, in the form of a lipid vesicle and/or remnant thereof comprising same, at at least one discrete locus and wherein the contacting is performed under conditions which would permit an agent, if present in the sample, to specifically bind to its corresponding lipid in the microarray; and (b) determining whether any known lipid in the microarray has an agent specifically bound thereto, thereby detecting the presence of the one or more agents in the sample.

This invention further provides a method for determining the amount of one or more agents in a sample, each of which specifically binds to one or more known lipids, which method comprises: (a) contacting the sample with the above microarrays, wherein each known lipid is affixed, in the form of a lipid vesicle and/or remnant thereof comprising same, at at least one discrete locus, and wherein the contacting is performed under conditions which would permit an agent, if present in the sample, to specifically bind to its corresponding lipid in the microarray; (b) for each known lipid in the microarray, determining the identity and amount of agent specifically bound thereto; and (c) comparing the identities and amounts so determined to a known standard, thereby determining the amount of the one or more agents in the sample.

This invention further provides a method for determining whether a subject is afflicted with a disorder characterized by the presence or absence in an afflicted subject of an agent which specifically binds to a known lipid, which method comprises: (a) contacting a suitable sample from the subject with the above microarrays, wherein the known lipid is affixed, in the form of a lipid vesicle and/or remnant thereof comprising same, at at least one discrete locus and wherein the contacting is performed under conditions which would permit the agent, if present in the sample, to specifically bind to the known lipid in the microarray; and (b) determining whether the known lipid in the microarray has the agent specifically bound thereto, thereby determining whether the subject is afflicted with the disorder.

This invention further provides a method for making an article of manufacture comprising a solid support having affixed to its surface a lipid vesicle and/or remnant thereof, which method comprises contacting the solid support with the lipid vesicle under suitable conditions.

This invention further provides two methods for making microarrays. The first method is for making a microarray comprising a solid support having affixed to its surface at discrete loci a plurality of lipid vesicles and/or remnants thereof, which method comprises contacting the solid support with the lipid vesicles under suitable conditions, whereby the composition of lipid vesicles and/or remnants thereof at each discrete locus differs from the composition of lipid vesicles and/or remnants thereof at at least one other discrete locus.

The second method is for making a microarray comprising a plurality of solid supports, each support having (i) one or a plurality of lipid vesicles and/or remnants thereof affixed to its surface at a single discrete locus or (ii) a plurality of lipid vesicles and/or remnants thereof affixed to its surface at discrete loci, which method comprises contacting the solid supports with the lipid vesicles under suitable conditions, whereby the composition of lipid vesicles and/or remnants thereof at each discrete locus differs from the composition of lipid vesicles and/or remnants thereof at at least one other discrete locus.

This invention also provides a second article of manufacture produced by the above method of making an article of manufacture.

This invention further provides a third microarray produced by the above first method of making a microarray.

This invention further provides a fourth microarray produced by the above second method of making a microarray.

This invention also provides kits which comprise the above articles of manufacture and microarrays and instructions for use.

Finally, this invention provides a kit for practicing the above method for determining whether a subject is afflicted with a disorder which comprises: (a) a microarray comprising a solid support having affixed to its surface at discrete loci a plurality of lipid vesicles and/or remnants thereof, wherein (i) at at least one discrete locus is affixed the lipid vesicle and/or remnant thereof to which the agent present or absent in an afflicted subject specifically binds, and (ii) the composition of lipid vesicles and/or remnants thereof at each discrete locus differs from the composition of lipid vesicles and/or remnants thereof at at least one other discrete locus; and (b) instructions for use.

BRIEF DESCRIPTION OF THE FIGURES

FIGS. 3A & 3B
These Figures show a "mini" platform of carbohydrate and lipid arrays which revealed natural antibody fingerprints on the chip surface, their strain-dependent and IgH-restricted characteristic profiles.
FIG. 3A shows images of stained microarrays.
FIG. 3B shows the contents of each "mini" array. The carbohydrate/lipid arrays display twelve distinct antigen preparations. Each preparation was printed in triplicate at each of four dilutions. IgM binding to the antigens spotted on the arrays is revealed by fluorochrome-coupled antibodies specific for either $IgM^a$ or $IgM^b$ allotype. Arrows mark α1,6-dextran and α1,6-dextran-stearylamine conjugate, the antigens that most clearly distinguish $IgM^a$ from $IgM^b$. Liposomes with various ratios of glycolipid and phosphatidylcholine (PtC) are spotted at other locations (See FIG. 3B). 2 μl of each serum diluted 1:25 was applied.

DETAILED DESCRIPTION OF THE INVENTION

Terms

Figure 1:
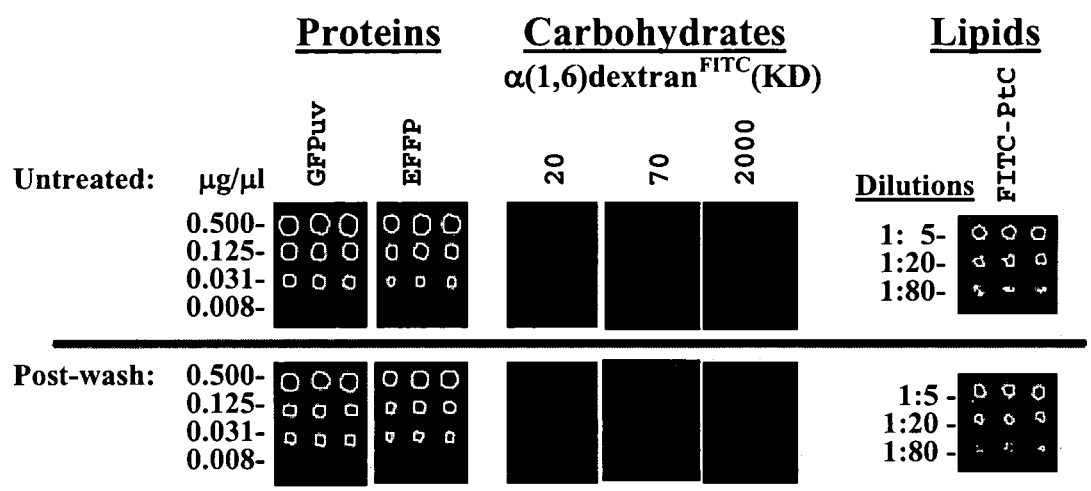
FIG. 1
This Figure shows a high-throughput biochip platform for constructing protein, carbohydrate and lipid microarrays.

"Affixed" shall mean attached by any means. In one embodiment, affixed shall mean attached by a covalent bond. In another embodiment, affixed shall mean attached non-covalently.

"Agent" shall mean any chemical or biological entity, including, without limitation, a cell, a glycomer, a lipid, a protein, an antibody, a lectin, a nucleic acid, a small molecule, and any combination thereof.

"Antibody" shall mean (a) an immunoglobulin molecule comprising two heavy chains and two light chains and which recognizes an antigen; (b) polyclonal and monoclonal immunoglobulin molecules; and (c) monovalent and divalent fragments thereof. Immunoglobulin molecules may derive from any of the commonly known classes, including but not limited to IgA, secretory IgA, IgG and IgM. IgG subclasses are also well known to those in the art and include, but are not limited to, human IgG1, IgG2, IgG3 and IgG4. Antibodies can be both naturally occurring and non-naturally occurring. Furthermore, antibodies include chimeric antibodies, wholly synthetic antibodies, single chain antibodies, and fragments thereof. Antibodies may be human or nonhuman. Nonhuman antibodies may be humanized by recombinant methods to reduce their immunogenicity in man.

"Aqueous solution" shall mean any solution in which water is a solvent. Examples of aqueous solutions include water and water-based buffer solutions.

"Complex carbohydrate" shall mean a carbohydrate polymer comprising more than two types of saccharide monomer units. Examples of complex carbohydrates include blood group substances such as Lewis X and Lewis Y.

"Composition of lipid vesicles" at a discrete locus shall mean the identity of the one or more lipid vesicles at that locus. For example, if locus 1 has lipid vesicles A and B, and locus 2 has lipid vesicles A and C, then the composition of lipid vesicles at locus 1 differs from that at locus 2.

"Compound" shall mean any molecule. Compounds include, but are not limited to, proteins, nucleic acids, glycomers, lipids and small molecules.

"Discrete locus" shall mean a point, region or area for the affixation of a lipid vesicle or remnant thereof, or other agent, which does not overlap with another such point, region or area, and which may further be separated from another such point, region or area by physical space.

"Glycomer" shall mean any carbohydrate-containing moiety. Glycomers include, without limitation, (a) complex carbohydrates, (b) polysaccharides, (c) oligosaccharides and (d) glycoconjugates. "Glycoconjugates" include, without limitation, glycoproteins, glycolipids and glycopolymers. In one embodiment of the glycomer, the carbohydrate moiety thereof is conjugated, either covalently or noncovalently, to polyacrylamide.

"Insoluble protein" shall mean any protein which does not solubilize in aqueous solution. Examples of insoluble proteins include trans-membrane proteins.

"Known standard", for the purpose of qualitative or quantitative comparison, can exist, for example, as data from an internal experimental control, or data from an external experimental control performed before, during or after the determination for which it is used. For example, in a method for determining the amount of an antibody in a sample which binds to lipid X, a known standard can be data (e.g., a lipid microarray density measurement) obtained by measuring a lipid X-containing microarray which has been contacted with a predetermined amount of the antibody.

"Lectin" shall mean a protein that is capable of agglutinating erythrocytes, binding sugars, and/or stimulating mitosis. Examples of lectins include concavalin A.

"Lipid vesicle" includes, without limitation, a liposome and a micelle. Further, a lipid vesicle can have integrated therein a fragment of lipid membrane (e.g. a cell or organelle membrane).

"Microarray" shall mean (a) a solid support having one or more entities affixed to its surface at discrete loci, or (b) a plurality of solid supports, each support having one or a plurality of entities affixed to its surface at discrete loci. The instant microarrays can contain all possible permutations of entities within the parameters of this invention. For example, the instant microarray can be an all-lipid microarray, a microarray with a plurality of compounds, a microarray with a plurality of compounds including lipid vesicles, a disease-specific microarray, a species-specific microarray, or a tissue-specific microarray.

"Nitrocellulose or Hydrogel support" shall mean any solid support having nitrocellulose or Hydrogel affixed to its surface. Nitrocellulose or Hydrogel supports include, without limitation, nitrocellulose-coated or Hydrogel-coated chips (e.g. silicone chips), slides (e.g. glass slides), filters, plates and beads.

"Polysaccharide" shall mean a carbohydrate polymer comprising either one or two types of saccharide monomer units. Examples of polysaccharides include bacterial cell surface carbohydrates.

"Remnant" of a lipid vesicle shall mean material which remains after the destruction of the vesicle. Such material includes (i) all or a portion of the vesicles' membrane, (ii) individual lipids of which the vesicle was made, (iii) a combination of (i) and (ii).

"Sample", when used in connection with the instant methods, includes, but is not limited to, any body tissue, skin lesion, blood, serum, plasma, cerebrospinal fluid, lymphocyte, urine, exudate, or supernatant from a cell culture.

"Specifically bind" shall mean the binding of a first entity to a second entity based on complementarity between the three-dimensional structures of each. In one embodiment, specific binding occurs with a $K_D$ of less than $10^{-5}$. In another embodiment, specific binding occurs with a $K_D$ of less than $10^{-8}$. In a further embodiment, specific binding occurs with a $K_D$ of less than $10^{-11}$.

"Subject" shall mean any organism including, without limitation, a mouse, a rat, a dog, a guinea pig, a ferret, a rabbit and a primate. In the preferred embodiment, the subject is a human being.

"Type", as used with respect to a lipid, means identity. Thus, for two lipids to be of the same type, they must be identical.

Embodiments of the Invention

This invention provides two articles of manufacture and four microarrays. The first article of manufacture comprises a solid support having affixed to its surface at a single locus one or more lipid vesicles and/or remnants thereof.

In one embodiment of the first article, the solid support is nitrocellulose or Hydrogel. In another embodiment, the solid support is selected from the group consisting of a chip, a slide, a filter, a bead and a plate. In another embodiment, each lipid vesicle and/or remnant thereof is made of only one type of lipid. In another embodiment, each lipid vesicle and/or remnant thereof is made of a plurality of types of lipids. In a further embodiment, the lipid vesicle is a liposome.

The first microarray comprises a solid support having affixed to its surface at discrete loci a plurality of lipid vesicles and/or remnants thereof, wherein the composition of lipid vesicles and/or remnants thereof at each discrete locus differs from the composition of lipid vesicles and/or remnants thereof at at least one other discrete locus.

The second microarray comprises a plurality of solid supports, each support having (i) one or a plurality of lipid vesicles and/or remnants thereof affixed to its surface at a single discrete locus or (ii) a plurality of lipid vesicles and/or remnants thereof affixed to its surface at discrete loci, wherein the composition of lipid vesicles and/or remnants thereof at each discrete locus differs from the composition of lipid vesicles and/or remnants thereof at at least one other discrete locus.

In one embodiment of the first and second microarrays, the solid support is nitrocellulose or Hydrogel. In another embodiment, the solid support is selected from the group consisting of a chip, a slide, a filter, a bead and a plate.

In one embodiment of the first and second microarrays, each lipid vesicle and/or remnant thereof is made of only one type of lipid. In another embodiment, each lipid vesicle and/or remnant thereof is made of a plurality of types of lipids. In a further embodiment, the lipid vesicle is a liposome.

In one embodiment of the first and second microarrays, the number of discrete loci is at least 100. In another embodiment, the number of discrete loci is at least 1000. In a further embodiment, the number of discrete loci is at least 10,000.

In one embodiment of the first and second microarrays, at each locus is affixed only one type of lipid vesicle and/or remnant thereof. In one embodiment, at at least one locus is affixed a plurality of types of lipid vesicles and/or remnants thereof. In another embodiment, the microarray further has affixed to its surface one or more compounds selected from the group consisting of a glycomer, an insoluble protein, a lectin and an antibody. In a further embodiment, the microarray further has affixed to its surface one or more compounds selected from the group consisting of a soluble protein, a nucleic acid and a small molecule.

This invention also provides a method for detecting in a sample the presence of one or more agents which specifically bind to one or more known lipids, which method comprises: (a) contacting the sample with the above microarrays, wherein each known lipid is affixed, in the form of a lipid vesicle and/or remnant thereof comprising same, at at least one discrete locus and wherein the contacting is performed under conditions which would permit an agent, if present in the sample, to specifically bind to its corresponding lipid in the microarray; and (b) determining whether any known lipid in the microarray has an agent specifically bound thereto, thereby detecting the presence of the one or more agents in the sample.

In one embodiment of the above method, the agent is an antibody. In another embodiment, the presence of the antibody in the sample correlates with an inflammatory disease or susceptibility thereto in the subject. In another embodiment, the presence of the antibody in the sample correlates with an infection, an infectious disease, or susceptibility thereto in the subject. In another embodiment, the presence of the antibody in the sample correlates with an autoimmune disease or susceptibility thereto in the subject. In another embodiment, the presence of the antibody in the sample correlates with the presence of a tumor in the subject. In another embodiment, the presence of the antibody in the sample correlates with a metabolic disease or pathogenic process or susceptibility thereto in the subject. In another embodiment, the presence of the antibody in the sample correlates with atherogenesis or cardiovascular disease or susceptibility thereto in the subject. In another embodiment, the presence of the antibody in the sample correlates with a genetic disease, a genetic defect or a genetic trait in the subject.

In one embodiment of the above method, the method comprises detecting the presence of a plurality of agents in the sample, each of which binds to a plurality of lipids. In another embodiment, the method comprises detecting the presence of a plurality of agents in the sample, each of which binds to one lipid.

In one embodiment of the above method, the lipid vesicle is a liposome.

This invention further provides a method for determining the amount of one or more agents in a sample, each of which specifically binds to one or more known lipids, which method comprises: (a) contacting the sample with the above microarrays, wherein each known lipid is affixed, in the form of a lipid vesicle and/or remnant thereof comprising same, at at least one discrete locus, and wherein the contacting is performed under conditions which would permit an agent, if present in the sample, to specifically bind to its corresponding lipid in the microarray; (b) for each known lipid in the microarray, determining the identity and amount of agent specifically bound thereto; and (c) comparing the identities and amounts so determined to a known standard, thereby determining the amount of the one or more agents in the sample.

"Determining" whether an agent is bound to a compound in a microarray can be performed according to methods well known in the art. Such methods include, but are not limited to, fluorescence, radioimmunoassay, and immunolabeling detection.

In one embodiment of the above method, the agent is an antibody.

In another embodiment of the above method, a predetermined amount of the antibody in the sample correlates with an inflammatory disease or susceptibility thereto in the subject.

In another embodiment, a predetermined amount of the antibody in the sample correlates with an infection or susceptibility thereto in the subject. In another embodiment, a predetermined amount of the antibody in the sample correlates with an autoimmune disease or susceptibility thereto in the subject. In another embodiment, a predetermined amount of the antibody in the sample correlates with the presence of a tumor or susceptibility thereto in the subject.

In one embodiment of the above method, the method comprises determining the amount of each of a plurality of agents in the sample, each of which binds to a plurality of lipids. In another embodiment, the method comprises determining the amount of each of a plurality of agents in the sample, each of which binds to one lipid.

In one embodiment of the above method, the lipid vesicle is a liposome.

This invention further provides a method for determining whether a subject is afflicted with a disorder characterized by the presence or absence in an afflicted subject of an agent which specifically binds to a known lipid, which method comprises: (a) contacting a suitable sample from the subject with the above microarrays, wherein the known lipid is affixed, in the form of a lipid vesicle and/or remnant thereof comprising same, at at least one discrete locus and wherein the contacting is performed under conditions which would permit the agent, if present in the sample, to specifically bind to the known lipid in the microarray; and (b) determining whether the known lipid in the microarray has the agent specifically bound thereto, thereby determining whether the subject is afflicted with the disorder.

In one embodiment of the above method, the subject is human. In another embodiment, the disorder is selected from the group consisting of an inflammatory disorder, an infection, an autoimmune disease, or a tumor. In a further embodiment, the lipid vesicle is a liposome.

This invention provides a method for making an article of manufacture comprising a solid support having affixed to its surface a lipid vesicle and/or remnant thereof, which method comprises contacting the solid support with the lipid vesicle under suitable conditions.

In one embodiment of the above method, the solid support is nitrocellulose or Hydrogel. In another embodiment, the solid support is selected from the group consisting of a chip, a slide, a filter, a bead and a plate.

In one embodiment of the above method, each lipid vesicle and/or remnant thereof is made of only one type of lipid. In another embodiment, each lipid vesicle and/or remnant thereof is made of a plurality of types of lipids. In a further embodiment, the lipid vesicle is a liposome.

This invention also provides two methods for making microarrays. The first method is for making a microarray comprising a solid support having affixed to its surface at discrete loci a plurality of lipid vesicles and/or remnants thereof, which method comprises contacting the solid support with the lipid vesicles under suitable conditions, whereby the composition of lipid vesicles and/or remnants thereof at each discrete locus differs from the composition of lipid vesicles and/or remnants thereof at at least one other discrete locus.

The second method is for making a microarray comprising a plurality of solid supports, each support having (i) one or a plurality of lipid vesicles and/or remnants thereof affixed to its surface at a single discrete locus or (ii) a plurality of lipid vesicles and/or remnants thereof affixed to its surface at discrete loci, which method comprises contacting the solid supports with the lipid vesicles under suitable conditions, whereby the composition of lipid vesicles and/or remnants thereof at each discrete locus differs from the composition of lipid vesicles and/or remnants thereof at at least one other discrete locus.

In one embodiment of the above methods, the solid support is nitrocellulose or Hydrogel. In another embodiment, the solid support is selected from the group consisting of a chip, a slide, a filter, a bead and a plate.

In one embodiment of the above methods, each lipid vesicle and/or remnant thereof is made of only one type of lipid. In another embodiment, each lipid vesicle and/or remnant thereof is made of a plurality of types of lipids.

In one embodiment of the above methods, the number of discrete loci is at least 100. In another embodiment, the number of discrete loci is at least 1000. In a further embodiment, the number of discrete loci is at least 10,000.

In one embodiment of the above methods, at each locus is affixed only one type of lipid vesicle and/or remnants thereof. In another embodiment, at at least one locus is affixed a plurality of types of lipid vesicles and/or remnants thereof.

In one embodiment of the above methods, the microarray further has affixed to its surface one or more compounds selected from the group consisting of a glycomer, an insoluble protein, a lectin and an antibody. In another embodiment, the microarray further has affixed to its surface one or more compounds selected from the group consisting of a soluble protein, a nucleic acid and a small molecule.

In one embodiment of the above methods, the lipid vesicle is a liposome.

This invention further provides a second article of manufacture produced by the above method of making an article of manufacture. This invention also provides a third microarray produced by the above first method of making a microarray. This invention also provides a fourth microarray produced by the above second method of making a microarray.

This invention provides a kit which comprises one of the above articles of manufacture and instructions for use.

This invention also provides a kit which comprises one of the above microarrays and instructions for use.

This invention further provides a kit which comprises One of the above articles of manufacture and a dessicant.

This invention provides a kit which comprises one of the above microarrays and a desiccant.

This invention further provides a kit which comprises one of the above articles of manufacture immersed in an aqueous solution.

This invention further provides a kit which comprises one of the above microarrays immersed in an aqueous solution.

Finally, this invention provides a kit for practicing the above method for determining whether a subject is afflicted with a disorder which comprises: (a) a microarray comprising a solid support having affixed to its surface at discrete loci a plurality of lipid vesicles and/or remnants thereof, wherein (i) at at least one discrete locus is affixed the lipid vesicle and/or remnant thereof to which the agent present or absent in an afflicted subject specifically binds, and (ii) the composition of lipid vesicles and/or remnants thereof at each discrete locus differs from the composition of lipid vesicles and/or remnants thereof at at least one other discrete locus; and (b) instructions for use.

In one embodiment of the above kit, the lipid vesicle is a liposome.

Examples of lipids are set forth below. In no way are these examples intended to limit the scope of lipids useful in connection with this invention.

Natural lipids include, for example, Lipid A (Detoxified Lipid A), Cholesterol, Sphingolipids (Spingosine and Derivatives such as D-erythro-Sphingosine, Sphingomyelin, Ceramides, Cerebrosides, Brain Sulfatides), Gangliosides, Sphingosine Derivatives (Glucosylceramide), Phytosphingosine and Derivatives (Phytosphingosine, D-ribo-Phytosphingosine -1-Phosphate, N-Acyl Phytosphingosine C2, N-Acyl Phytosphingosine C8, N-Acyl Phytosphingosine C18), Choline (Phosphatidylcholine, Platelet-Activation Factor), Ethanolamine (Phosphatidylethanolamine), Glycerol (Phosphatidyl-DL-glycerol), Inositol (Phosphatidylinositol, Phosphatidylinositol, Serine (Phosphatidylserine (sodium salt)), Cardiolipin, Phosphatidic Acid, Egg Derived (Egg Derivatives), Lyso (Mono Acyl) Derivatives (Lysophosphatides), Hydrogenated Phospholipids, Lipid Tissue Extracts (Brain & Egg, Escherichia Coli & Heart, Liver & Soy), and Fatty Acid Content of Tissue Derived Phosolipids (Phosphatidylcholine, Phosphatidylethanolamine).

Sphingolipids include, for example, Sphingosine (D-erythro Sphingosine, Sphingosine-l-Phosphate, N,N-Dimethylsphingosine, N,N,N,-Trimethylspingosine, Sphingosylphosphorylcholine, Sphingomyelin, Glycosylated Sphingosine), Ceramide Derivatives (Ceramids, D-erythro Cermaid-l-Phosphate, Glycosulated Ceramids), Sphinganine (Dihydrosphingosine)(Sphinganine-1-Phosphate, Sphinganine (C20), D-erythro Sphinganine, N-Acyl-Sphinganine C2, N-Acyl-Sphinganine C8, N-Acyl-Sphinganine C16, N-Acyl-Sphinganine C18, N-Acyl-Sphinganine C24, N-Acyl-Sphinganine C24:1, Glycosylated (C18) Sphingosine and Phospholipid Derivatives (Glycosylated-Sphingosine) (Sphingosine, βD-Glucosyl, Sphingosine, βD-Galactosyl, Sphingosine, βD-Lactosyl),Glycosylated-Ceramide (D-Glucosyl-β1-1'Ceramide (C8), D-Galactosyl-β1-1' Ceramide (C8), D-Lactosyl-β1-1' Ceramide (C8), D-Glucosyl-β1-1' Ceramide (C12), D-Galactosyl-β1-1' Ceramide (C12), D-Lactosyl-β1-1' Ceramide (C12)), Glycosylated-Phosphatidylethanolamine(1,2-Dioleoyl-sn-Glycero-3-Phosphoethanolamine-N-Lactose), D-erythro (C17) Derivatives (D-erythro Sphingosine, D-erythro Sphingosine-1-phosphate), D-erythro (C20) Derivatives (D-erythro Sphingosine), and L-threo (C18) Derivatives (L-threo Spingosine, Safingol (L-threo Dihydrosphingosine)).

Synthetic Glycerol-Based Lipids include, for example, Phosphaditylcholine, Phosphatidylethanolamine, Phosphatidylserine, Phosphatidylinositol, Phosphatidic Acid, Phosphatidylglycerol, Cardiolipin, Diacylglycerides, Cholesterol, PEG Lipids, Functionalized Lipids for Conjugation, Phospholipids with Multifarious Headgroups, Lipids for pH Sensitive Liposomes, Metal Chelating Lipids, Antigenic Phospholipids, Doxyl Lipids, Fluorescent Lipids, Lyso Phospholipids, Alkyl Phosphocholine, Oxidized Lipids, Biotinylated, Ether Lipids, Plasmologen Lipids, Diphytanoyl Phospholipids, Polymerizable Lipids, Brominated Phospholipids, Fluorinated Phospholipids, Deuterated Lipids, Doxyl Lipids, Fluorescent Lipids, Enzyme Activators (DG, PS), Enzyme Inhibitors (v-CAM, Inhibitor of PKC), Bioactive Glycerol-Based Lipids (Platelet Activation Factor Lipids, Second Messenger Lipids), Lipid Metabolic Intermediates (Acyl Coenzyme A, CDP-Diacylglycerol, and VPC-G protein-coupled receptor (LPA$_1$/LPA$_3$ Receptor Antagonist, LPA Receptor Agonist, S1P$_1$/S1P$_3$ Receptor Antagonist, S1P$_1$/S1P$_3$ Receptor Agonist).

Ether Lipids include, for example, Diether Lipids (Dialkyl Phosphatidylcholine, Diphytanyl Ether Lipids), Alkyl Phosphocholine (Dodedylphosphocholine), O-Alkyl diacylphosphatidylcholinium (1,2-Diacyl-sn-Glycero-3-Phosphocholine & Derivatives), and Synthetic PAF and Derivatives (1-Alkyl-2-Acyl-Glycerol-3-Phosphocholine and Derivatives).

Polymers & Polymerizable Lipids include, for example, Diacetylene Phospholipids, mPEG Phospholipids and mPEG Ceramides (Poly(ethylene glycol)-Lipid Conjugates, mPeg 350 PE, mPEG 550 PE, mPEG 750 PE, mPEG 1000 PE, mPEG 2000 PE, mPEG 3000 PE, mPEG 5000 PE, mPEG 750 Ceramide, mPEG 2000 Ceramide, mPEG 5000 Ceramide), and Functionalized PEG Lipids.

Fluorescent Lipids include, for example, Fatty Acid Labeled Lipids that are Glycerol Based (Phosphatidylcholine, Phosphatidic Acid, Phosphatidylethanolamine, Phosphatidylglycerol, Phosphatidylserine) and Sphingosine Based (Sphingosine, Sphingosine-1-Phosphate, Ceramide, Sphingomyelin, Phytosphingosine, Galactosyl Cerebroside), Headgroup Labeled Lipids (Phosphatidylethanolamine, Phosphatidylethanolamine, Dioleoyl Phosphatidylethanolamine, Phosphatidylserine, Phosphatidylserine), and 25-NBD Cholesterol.

Oxidized Lipids include, for example, 1-Palmitoyl-2-Azelaoyl-sn-Glycero-Phosphocholine, 1-O-Hexadecyl-2-Azeolaoyl-sn-Glycero-3-Phosphocholine, 1-Palmitoyl-2-Glutaroly-sn-Glycero-3-Phosphocholine, 1-Palmitoyl-2-(9'-oxo-Nonanoyl)-sn-Glycero-3-Phosphocholine, and 1-Palmitoyl-2-(5'-oxo-Valeroyl)-sn-Glycero-3-Phosphocholine.

Finally, lipids include, for example, DLPC, DMPC, DPPC, DSPC, DOPC, DMPE, DPPE, DOPE, DMPA-Na, DPPA-Na, DOPA-Na, DMPG-Na, DPPG-Na, DOPG-Na, DMPS-Na, DPPS-Na, DOPS-Na, DOPE-Glutaryl-Na, Tetra Myristoyl Cardiolipin $(Na)_2$, DPPE-mPEG-2000-Na, DPPE-mPEG-5000-Na, DPPE Carboxy PEG 2000-Na and DOTAP-Cl.

This invention will be better understood from the Experimental Details that follow. However, one skilled in the art will readily appreciate that the specific methods and results discussed are merely illustrative of the invention as described more fully in the claims which follow thereafter.

Experimental Details
Synopsis

We report here the establishment of a liposome-based microarray technology in which lipid vesicles (liposomes) may be spotted ("printed") directly on nitrocellulose-coated glass microscope slides using existing cDNA microarray spotting technology. With this procedure, any substance that can form liposomes or can be incorporated into liposomes can be printed on the array. The lipids of the liposomes maintain their antigenic structure when printed on the array such that antibodies that react with these lipids bind to the printed molecules. The bound antibodies may be detectable directly, if they are labeled with fluorochromes or other molecular labels. Alternatively, the bound antibodies may be detected indirectly by their reaction with labeled anti immunoglobulin ("second-step") antibodies or other labeled molecules that specifically detect immunoglobulins. The facility with which lipids can be printed on arrays and maintained in this format for 6 months or longer enables the use of this technology for the creation of high-throughput micro- and macro-arrays and for the routine use of this technology for biomedical purposes.

Certain Advantages of the Invention

We developed lipid-based microarrays to explore the structural and antigenic diversities of lipid molecules and to facilitate the characterization of lipid-antibody interaction. Our laboratory has already developed a simple and highly efficient method for immobilization of carbohydrate and protein molecules on a nitrocellulose-coated micro-glass slide [17-20].

Most lipid molecules are only soluble in organic solvents and the existing micro-spotting devices were not designed to handle organic solvents. Neither the contact-quill pin systems-nor the non-contact arraying systems can be applied to uptake lipids that were dissolved in organic solvent and to release them quantitatively as micro-spots on the chip surface. Dr. Ten Feizi's group in London [21] applied electrospray MASS spectrometry for the production of glycolipid arrays. In essence, they dissolved glycolipids in organic solvent and then spray them onto nitrocellulose membrane to produce micro-bars or macro-spots of glycolipids. This method is useful for the low-throughput lipid array production but is not suitable for the high-throughput production of lipid microarrays. Thus, construction of lipid arrays represented a challenge to the field of microarray technology.

Experimental Approach

We describe here an innovative approach to overcome the technical difficulty in lipid array production. Specifically, we demonstrated that aqueous suspensions of lipid vesicles (in this case, liposomes) are suitable for lipid array construction using existing micro-spotting devices. Thus, any lipid-containing molecules/preparations, including purified natural products, synthetic lipid molecules and cell extracts that can form lipid vesicles such as liposomes or can be incorporated into them, are applicable for microarray construction following this procedure. We have experimentally demonstrated that:

1) Liposome suspensions can be spotted in consistent quantities on nitrocellulose-coated slides using the quill-pin-based micro-spotting device. Lipids may be soluble in the form of micelles, which are closed lipid monolayers with a fatty acid core and polar surface (in an aqueous solution). Methods of high energy sonication may produce liposomes, as well as micelles. Both are suitable for lipid array construction;

2) Liposomes composed of either a single lipid molecule or mixtures of different lipid molecules are applicable for lipid array construction with this procedure;

3) Lipid/liposome arrays were firmly immobilized on the nitrocellulose substrate and are resistant to multiple incubations with aqueous solutions. Solutions tested include a) saline (0.9% NaCl); b) 1×PBS, pH 7.4; c) 1×PBS, pH 7.4 with 0.05% Tween 20 and d) 1% BSA in 1×PBS, pH 7.4, 0.05% Tween 20;

4) The antigenic structures displayed by lipid/liposome arrays were detected by antibodies and/or lectins specific for corresponding phospholipid- or glycolipid-moieties; and 5) Lipid/liposome arrays that were air-dried and stored at RT for six months preserved their antigenic reactivities as detected by anti-lipids and anti-carbohydrate antibodies in a number of model systems.

I. Materials and Methods

Liposomes are one type of lipid vesicle. They are formed when thin lipid films or lipid cakes are hydrated and stacks of liquid crystalline bilayers become fluid and swell. The properties of lipids vary depending on the composition (cationic, anionic, neutral lipid species). However, the same preparation method can be used for all lipid vesicles regardless of composition. Two commonly used methods, sonication (sonic energy) and extrusion (mechanical energy), were tested. Both produced liposomes that are suitable for lipid array construction.

(A) Apparatus, Reagents and Buffers for SUV Preparation

Probe Sonicator: VirSonic 475 of VIRTIS or VWR Scientific.

Bath Sonicator: Model G112SPIG from Laboratory Supplies Co., Inc., 29 Jefry Lane, Hicksville, N.Y.).

Microspotting device: Cartesian Technologies' PIXSYS 5500C (Irvine, Calif.).

Supporting Substrate: Nitrocellulose-coated micro-glass slides (FAST Slides, Schleicher & Schuell, Keene, N.H.).

Microarray scanner: ScanArray 5000A Standard Biochip Scanning System (Packard Biochip Technologies, Inc., Billerica, Mass.).

Lipids: (See Table 1).

Dilution buffer: Saline [0.9% NaCl, 0.02% (w/v) sodium azide].

Rinsing solution: 1×PBS, pH 7.4 w/0.05% (vol/vol) Tween 20.

Blocking solution: 1% (wt/vol) BSA in PBS w/0.05% (wt/vol) $NaN_3$.

(B) Sonication to Produce Small, Unilamellar Vesicles (SUVs) for Array Construction In order to produce a diverse panel of liposomes for lipid array construction, we developed methods for small-scale but higher-throughput production of liposomes.

1. Method of Probe-sonication

Roger R. C. New's protocol [22] was applied with necessary modifications to produce SUVs that are relatively stable at 4° C. for the purpose of lipid array construction:

a) Dissolve 1 mg lipids in 100-500 microliters of chloroform or other proper organic solvents in a glass or a proper plastic vial. Mix it well by vortexing when multiple lipid components are applied;

b) Dry down the lipid solutions (chloroform) by speed-vacuum overnight or by method of nitrogen evaporation [22] followed by speed-vac;

c) Add 0.5 ml saline [0.9% NaCl, 0.02% (w/v) sodium azide] with or without aqueous soluble components (such as proteins, water-soluble ST-Dex, and other glycocojugates) to each vial (2 mg/ml);

d) Vortex tube vigorously to re-suspend the lipids in saline to generate a milky, uniform suspension;

e) Perform probe-sonication on ice until the lipid suspension becomes transparent. Usually, we sonicate a sample for 30" then cool it down on ice for 10", and repeat this cycle three times;

f) Spin the tubes at 10,000 g to remove insoluble substances that interfere with the micro-spotting procedure and use the homogenized transparent liposome suspensions for lipid array construction;

g) Store the liposomes at 4° C. before application. Most liposomes prepared by this procedure are stable as transparent suspension at 4° C. and can be applied for lipid array construction in two to three months. If insoluble precipitins appear in a preparation, repeat above steps "e-f" to treat the preparation. If transparent liposome suspension are obtained, test the preparation on chips for epitope display.

Note: To prevent oxidization of the lipid components, store spotted lipid arrays in an argon or nitrogen container.

2. Method of Bath-sonication

The general procedure is identical to the above method of probe sonication except that a bath sonicator (G112SPIG from Laboratory Supplies Co., Inc. or equivalent sonicators from Health Sonics Corporation, Livermore, Calif.) was applied to prepare multiple samples simultaneously. We follow the Morrissey Lab Protocol, as recommended by AVANTI Lipids, Inc.'s web site (www.avantilipids.com), for bath-sonication.

Note: Some lipids did not form a transparent liposome suspension by the bath-sonication. In these cases, we performed probe sonication as described in "Method of probe-sonication" above).

(C) Extrusion to Produce Large, Unilamellar Vesicles (LUVs)

Methods described by Mercolno et al. were applied to produce fluorescein-encapsulating liposomes. This method has been used to produce FITC-phosphotidylcholine (PtC) liposome for the purpose of cell surface staining. A preparation that stains the B cells producing anti-PtC antibodies was specifically tested for lipid array construction (FIG. 1).

II. EXAMPLES (A) A Practical Biochip Platform for Producing Protein, Carbohydrate and Lipid Microarrays 1. Materials and Methods Micro-spotting: GFPs, polysaccharides and liposomes were printed using Cartesian Technologies' PIXSYS 5500C (Irvine, Calif.) with STEALTH 3 pins.

Supporting substrate: FAST Slides (Schleicher & Schuell, Keene, N.H.). The printed carbohydrate microarrays were air dried and stored at room temperature before application.

Microarray-scanning: A ScanArray 5000 Standard Biochip Scanning System and its QuantArray software (Packard Biochip Technologies, Inc.) were applied for scanning and data capturing.

2. Results

We reported that a broad spectrum of carbohydrate-containing macromolecules that are hydrophilic in nature were stably immobilized on a nitrocellulose-coated glass slide and that the efficacy of antigen absorption depends largely on their molecular weights [17-20]. Given these findings, we further predicted that the aqueous-soluble proteins of suitable molecular mass could be immobilized on this surface without any pre-printing treatments. Given the knowledge that green flourescent proteins (GFPs) require preservation of their protein conformation in order to retain their fluorescing activities, two recombinant forms of the GFP [9], EGFP (enhanced GFP) and GFPuv (UV-optimized GFP variant), -were applied for this investigation. Detection of the signals that they generate provides a simple and efficient method to monitor their surface immobilization, as well as structural stability on-chip.

Results summarized in FIG. 1 showed that these GFP proteins were stably immobilized on the nitrocellulose slides and were fluorescing on-chip after air-drying, extensive washing and prolonged storage at room temperature. These properties are similar to those of FITC-labeled polysaccharides, as well as the Cy3- and Cy5-conjugates of Streptavidin that were printed and tested in the same experiments. These observations indicate that the bioarray platform we applied for printing carbohydrate arrays is suitable for the production of protein-based antigen arrays.

We further investigated whether this array platform is applicable to the lipid-based microarrays. Lipids are generally not water-soluble. Lipids dissolved in organic solvents are, however, not suitable for microarray construction. We tested, therefore, an alternative strategy to print a lipid array, i.e., spotting lipids in the form of liposomes. As seen in FIG. 1 (right column), a preparation of fluorescein-encapsulated liposome was printed on the same chip substrate on which we printed protein and carbohydrate. Its fluorescent signal is well-preserved after-air-drying and washing three times with 1×PBS, pH 7.4, containing 0.05% Tween 20.

(B) Liposomes as Vesicles to Deliver Glycolipids and to Facilitate the Surface-Display of Their Sugar Moieties on the Chip Surface Glycolipids are composed of hydrophobic lipid moieties and hydrophilic sugar chains. Immobilization of glycolipids via the hydrophobic-hydrophobic interaction on the nitrocellulose substrate may facilitate exposure of their hydrophilic saccharide moieties in the aqueous phase. Since each glycolipid displays only one sugar structure, use of glycolipid conjugates for the construction of a carbohydrate array is technically advanced in establishing epitope-specific glycan arrays. Therefore, we performed experiments to examine whether PtC liposomes can serve as vesicles to deliver glycolipid conjugates for spotting and to facilitate the surface-display of their sugar moieties on the chip surface. In design, we mixed GM1-glycolipid and egg PtC at 1:100 (20 ug/2 mg/ml saline) and 1:10 (200 ug/2 mg/ml saline) for liposome preparation. We stained the lipid/liposome arrays using an anti-GM1 rabbit anti-serum to detect the GM1 epitopes displayed.

Figure 2:
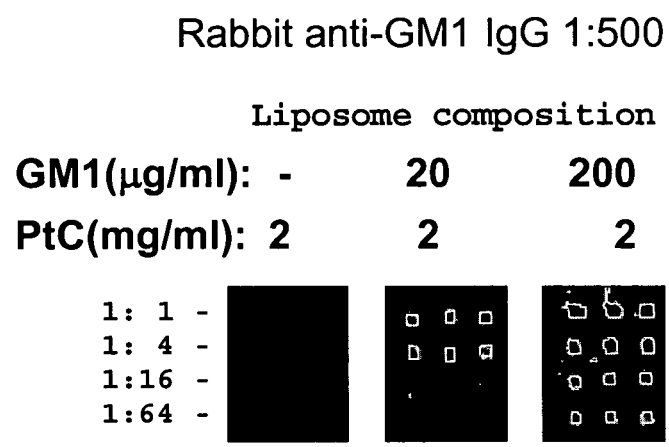
FIG. 2
This Figure shows quantitative detection of GM1-oligosaccharide displayed by liposome arrays.

Results presented in FIG. 2 showed clearly that a) the anti-GM1 antibody detected GM1 epitope in the arrays that contain the GM1-glycolipid but not the arrays without GM1-glycolipid; and b) the detected signals of GMl-epitope of the two GM1-containing arrays differ significantly. As expected, the GMl-high lipid array captured higher titers of anti-GM1 antibodies and the GM1-low lipid array captured lower titers of anti-GM1 antibodies. We conclude, therefore, that the use of liposomes as vesicles to deliver glycolipid conjugates for microarray construction is technically feasible. In addition, by varying the ratio of glycolipid and egg PtC in liposome preparation, we produced oligosaccharide arrays with different GM1-epitope densities. This represents a new class of glycan arrays that display single sugar chain epitopes with defined epitope-densities. Such oligosaccharide arrays are useful for probing the optimal cluster configuration of carbohydrate binding-sites of a given receptor, including antibody, lectin or lectin-like cellular receptor.

(C) Probing the Repertoire of Natural Antibodies Using Carbohydrate and Lipid Arrays One of the most important applications of this universal bioarray platform is for large-scale antibody profiling. In this experiment, we investigated whether this technology is suited for the detection of "natural" antibody (i.e., IgM), which is an integral part of the natural immunity that provides the first line of defense against invading pathogens.

Figure 3A:
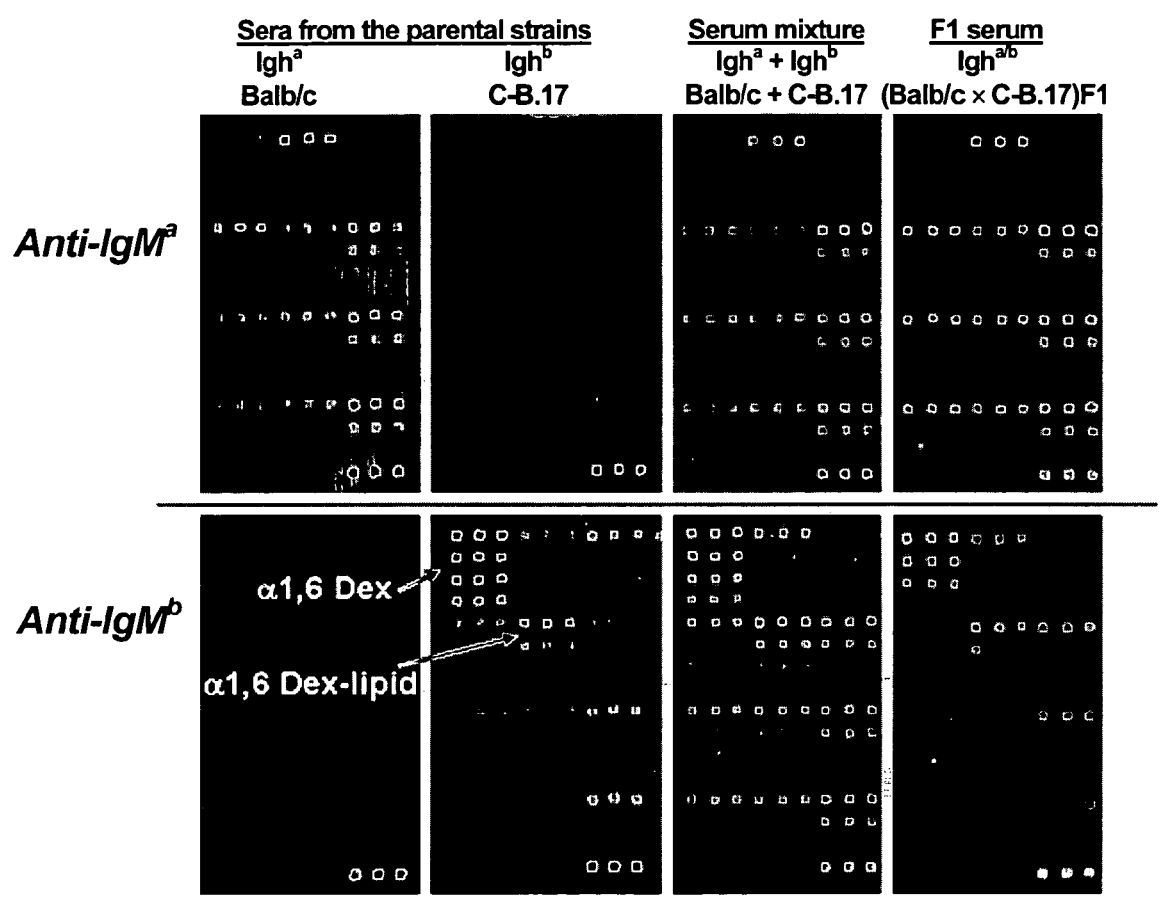

We constructed a "mini-array" that displays a panel of twelve carbohydrate and lipid antigens. FIG. 3 demonstrates that this bioarray platform has the level of detection sensitivity and specificity to monitor the natural antibodies in serum. Importantly, these initial studies have led to an important discovery that the natural antibody repertoire is under precise genetic control. Specifically, we have revealed sharp, reproducible differences between the reactivity patterns of the natural antibodies in congenic mice, BALB/c and C-B.17 sera, and shown that these differences are heritable and $IgV_H$-restricted in the F1 hybrid between these strains.

TABLE 1

Lipids

Tested Lipids

Stearylamine-α(1,6)dextran 70K (D. Wang Lab, Kabat Collection)
Stearylamine-Isomaltotriose (ST-IM3) (D. Wang Lab, Kabat Collection)
Stearylamine-Isomaltotetraose (ST-IM4) (D. Wang Lab, Kabat Collection)
Stearylamine-Isomaltopentaose (ST-IM5) (D. Wang Lab, Kabat Collection)
Distearoylphosophatidyl Choline (Avanti Polar lipids, Birmingham, AL)
Distearoylphosphatidyl Glycerol (Avanti Polar lipids, Birmingham, AL)
Cholesterol (Sigma Chemical Co., St. Louis, MO)
Ganglioside $G_{M1}$ (Avanti Polar lipids, Alabaster, AL)
L-α-Phosphatidylcholine (Egg, Chicken) (Avanti Polar lipids, Alabaster, AL)
Galb1,4GlcNACb1-HDPE (Type II chain unit) (V-LABS, INC, Louisiana US)
Gala1,3Galb1-HDPE (αGal-terminal di-saccharides) (V-LABS, INC, Louisiana US)
Gala1,3Galb1,4GlcNACb1-HDPE (αGal-trisaccharides) (V-LABS, INC, Louisiana US)
Cardiolipin (C1649) (Sigma Chemical Co., St. Louis, MO)

Untested Lipids (Avanti Polar Lipids, Inc.)

Total Ganglioside Extract (Brain, Porcine-Ammnium Salt)
D-erythro-Sphingosine (Egg, Chicken)
Sphingomyelin (Egg, Chicken), 10 MG/ML, Choroform 2.5 ML
L-α-phosphatidylglyderol (E. coli. Sodium Sale) 10 mg/ml 1 ml
Phytosphingosine (Saccharomyces cervisiae) 4-Hydroxysphinganine
Glucocerebrosides (Soy, 98%)
Sufatides (Brain, Porcine) (Cerebroside sulfates)
1.2-Dioleyl-sn-Glycero-3-phosphoethanolamine-N-(5-dimethylamino-1-naphthalenesulfenyl), 1 mg/ml chloroform 1 ml
Sphigomyelin (Milk, bovine), 10 mg/ml, chloroform 2.5 ml
Ceramide (Brain, Porcine)
Total Cerebrosides (Brain, Porcinel)
1,1',2,2'-Tetra,yristoyl Cardiolipin (Ammonium Salt), 10 mg/ml chloroform 2.5 ml
1,2-Dipalmitoyl-sn-Glycero-3-Phosphoethanolamime-N-[Methoxy(polyethylene glycol)-5000] (Ammonium Salt), 10 mg/ml chloroform 2.5 ml
1,2-Dioleoyl-3-Trimethylammonium-Propane (chloride Salt) (DOTAP), 10 mg/ml chloroform 2.5
1-Myristoyl-2-[12-[(7-mitro-2-1,3-benzoxadiazol-4-yl)amino]dodecanoyl]-sn-Glycero-3-phosphocholine, 1 mg/ml chloroform lml
L-α-phosphatidylserine (Brain, Poroine), (Sodium Sale)
Cardiolipin (heart, bovin-Disodium Salt), 10 mg/ml chloroform 2.5 ml
L-α-phosphatidic Acid (Egg, Chiken_Monosodium Salt), 10 mg/ml chloroform 2.5 ml
Brain total Lipid Extract, 25 mg/ml chloroform 4 ml
Brain Polar Lipid Extract (porcine), 25 MG/ML Choroform 4 ml
1,2-Dimyristoyl-sn-Glycero-3-phosphate (Monododium Salt) (DMPA), 10 MG/ML Chloroform 2.5 ml
1,2-Dimyristoyl-sn-Glycero-3-[phospho-rac-(1-glycerol)] (Sodium Salt) (DMPG), 10 MG/ML Choroform 2.5 ml
1,2-Dimyristoyl-sn-Glycero-3-[phospho-L-serine](Sodium Salt) (DMPS)

TABLE 1-continued

Lipids 1,2-Distearoyl-sn-Glycero-3-phosphecholine (DSPC), 10 mg/ml cholorform 2.5 ml
1,2-Dioleoyl-sn-glycero-3-phosphocholine (DOPC), 10 mg/ml chloroform 2.5 ml
1,2-Dimyristoyl-sn-Glycero-a-phosohoethanolamine (DMPE), 10 MG/ML Chforoform 2.5 ml
1,2-Dilauroyl-sn-glycero-3-phosphocholine (ELPC), 10 mg/ml Chloroform 2.5 ml
1,2-Dimyristoyl-sn-Glycero-3-phosphate (Monododium Salt) (DMPA), 10 MG/ML Chloroform 2.5 ml
1,2-dipalmitoyl-sn-Glycero-3-phosphocholine (oppc), 10 mg/ml Chloroform 2.5 ml

*HDPE: Neoglycolipids-1,2-di-O-hexadecyl-sn-glycero-3-phosphoethanolamine

REFERENCES

1. Hava, D. L., et al., *CD1 assembly and the formation of CD1-antigen complexes*. Curr Opin Immunol, 2005. 17(1): p. 88-94.
2. Van Kaer, L., *Regulation of immune responses by CD1d-restricted natural killer T cells*. Immunol Res, 2004. 30(2): p. 139-53.
3. Misasi, R., et al., *Gangliosides and autoimmune diabetes*. Diabetes Metab Rev, 1997. 13(3): p. 163-79.
4. Moran, A. P. and M. M. Prendergast, *Molecular mimicry in Campylobacter jejuni and Helicobacter pylori lipopolysaccharides: contribution of gastrointestinal infections to autoimmunity*. J Autoimmun, 2001. 16(3): p. 241-56.
5. Singh, A. K., et al., *Natural killer T cell activation protects mice against experimental autoimmune encephalomyelitis*. J Exp Med, 2001. 194(12): p. 1801-11.
6. Nojima, J., et al., *Strong correlation between the prevalence of cerebral infarction and the presence of anti-cardiolipin/beta2-glycoprotein I and anti-phosphatidylserine/prothrombin antibodies--Co-existence of these antibodies enhances ADP-induced platelet activation in vitro*. Thromb Haemost, 2004. 91(5): p. 967-76.
7. Robinson, W. H., et al., *Protein microarrays guide tolerizing DNA vaccine treatment of autoimmune encephalomyelitis*. Nat Biotechnol, 2003. 21(9): p. 1033-9.
8. Pedotti, R., et al., *Severe anaphylactic reactions to glutamic acid decarboxylase (GAD) self peptides in NOD mice that spontaneously develop autoimmune type 1 diabetes mellitus*. BMC Immunol, 2003. 4(1): p. 2.
9. Pedotti, R., et al., *Multiple elements of the allergic arm of the immune response modulate autoimmune demyelination*. Proc Natl Acad Sci U S A, 2003. 100(4): p. 1867-72.
10. Merrill, J. E., M. C. Graves, and D. G. Mulder, *Autoimmune disease and the nervous system. Biochemical, molecular, and clinical update*. West J Med, 1992. 156(6): p. 639-46.
11. Horkko, S., et al., *Immunological responses to oxidized LDL*. Free Radic Biol Med, 2000. 28(12): p. 1771-9.
12. Shaw, P. X., et al., *The autoreactivity of anti-phosphorylcholine antibodies for atherosclerosis-associated neo-antigens and apoptotic cells*. J Immunol, 2003. 170(12): p. 6151-7.
13. Moran, A. P., M. M. Prendergast, and B. J. Appelmelk, *Molecular mimicry of host structures by bacterial lipopolysaccharides and its contribution to disease*. FEMS Immunol Med Microbiol, 1996. 16(2): p. 105-15.
14. Chang, M. K., et al., *Apoptotic cells with oxidation-specific epitopes are immunogenic and proinflammatory*. J Exp Med, 2004. 200(11): p. 1359-70.
15. Binder, C. J., et al., *Pneumococcal vaccination decreases atherosclerotic lesion formation: molecular mimicry between Streptococcus pneumoniae and oxidized LDL*. Nat Med, 2003. 9(6): p. 736-43.
16. Howe, C. L., et al., *Antiapoptotic signaling by a remyelination-promoting human antimyelin antibody*. Neurobiol Dis, 2004. 15(1): p. 120-31.
17. Wang, D., *Carbohydrate microarrays*. Proteomics, 2003. 3: p. 2167-2175.
18. Wang, D., *Carbohydrate Antigens*. In: Encyclopedia of Molecular Cell Biology and Molecular Medicine, (ed. Robert A. Meyers), 2004. II: p. 277-301.
19. Wang, D., et al., *Carbohydrate microarrays for the recognition of cross-reactive molecular markers of microbes and host cells*. Nat Biotechnol, 2002. 20(3): p. 275-81.
20. Wang, D. and J. Lu, *Glycan arrays lead to the discovery of autoimmunogenic activity of SARS-COV*. Physiol Genomics, 2004. 18(2): p. 245-8.
21. Fukui, S., et al., *Oligosaccharide microarrays for high-throughput detection and specificity assignments of carbohydrate-protein interactions*. Nat Biotechnol, 2002. 20(10): p. 1011-7.
22. New, R. R. C., *Preparation of liposomes*, in *Liposomes A Practical Approach*, R. R. C. New, Editor. 2000, PAS. p. 33-103.

What is claimed is:

1. A microarray comprising a solid support comprising a surface coated with nitrocellulose wherein printed directly on the nitrocellulose at discrete loci are liposomes comprising glycolipids, wherein each locus comprises a distinct glycolipid antigenically distinct from the glycolipids of the other loci, the liposomes are directly immobilized at the loci via hydrophobic-hydrophobic interaction with the nitrocellulose, wherein the microarray has antibody detection sensitivity and specificity sufficient to reveal differences between reactivity patterns of natural IgM antibodies in congenic mice, BALB/c and C-B17 sera, wherein retention of the glycolipids on the nitrocellulose is resistant to incubation in aqueous solution, and the antigenic distinctiveness of the glycolipids is tolerant of air drying and storage at room temperature.

2. A microarray of oligosaccharides useful for probing cluster configuration of carbohydrate binding-sites of antibodies, wherein the microarray comprises liposomes comprising glycolipids comprising the oligosaccharides, and the liposomes are printed directly, and in an array of spots, on nitrocellulose-coated glass slides, wherein each spot comprises an antigenically distinct glycolipid of the glycolipids, the liposomes directly immobilized at the spots via hydrophobic-hydrophobic interaction with the nitrocellulose, wherein the glycolipids maintain their antigenic structures such that antibodies specific for the glycolipids bind the glycolipids of the printed liposomes sufficient to reveal differences between reactivity patterns of natural IgM antibodies in congenic mice, BALB/c and C-B17 sera, wherein retention of the glycolipids on the nitrocellulose is resistant to incubation in aqueous solution, and the antigenic distinctiveness of the glycolipids is tolerant of air drying and storage at room temperature.

3. The microarray of claim 1 wherein the glycolipids comprise each of:
Stearylamine-Isomaltotriose (ST-IM3);
Stearylamine-Isomaltotetraose (ST-IM4);
Stearylamine-Isomaltopentaose (ST-IM5);
Stearylamine-$\alpha$(1,6)dextran (ST-Dex);
Monosialotetrahexosylganglioside (GM1);
Gal$\beta$1,4GlcNAC$\beta$1-HDPE (NGL201);
Gal$\alpha$1,3Gal$\beta$1,4GlcNAC$\beta$1-HDPE (NGL203); and
Gal$\alpha$1,3Gal$\beta$1-HDPE (NGL334),
wherein HDPE is 1,2-di-O-hexadecyl-sn-glycero-3-phosphoethanolamine.

4. The microarray of claim 2 wherein the glycolipids comprise each of:
Stearylamine-Isomaltotriose (ST-IM3);
Stearylamine-Isomaltotetraose (ST-IM4);
Stearylamine-Isomaltopentaose (ST-IM5);
Stearylamine-$\alpha$(1,6)dextran (ST-Dex);
Monosialotetrahexosylganglioside (GM1);
Gal$\beta$1,4GlcNAC$\beta$1-HDPE (NGL201);
Gal$\alpha$1,3Gal$\beta$1,4GlcNAC$\beta$1-HDPE (NGL203); and
Gal$\alpha$1,3Gal$\beta$1-HDPE (NGL334),
wherein HDPE is 1,2-di-O-hexadecyl-sn-glycero-3-phosphoethanolamine.

5. The microarray of claim 1 wherein the liposomes further comprise L-$\alpha$-phosphatidylcholine (PTC).

6. The microarray of claim 2 wherein the liposomes further comprise L-$\alpha$-phosphatidylcholine (PTC).

7. The microarray of claim 3 wherein the liposomes further comprise L-$\alpha$-phosphatidylcholine (PTC).

8. The microarray of claim 4 wherein the liposomes further comprise L-$\alpha$-phosphatidylcholine (PTC).

9. The microarray of claim 1 wherein specifically bound to the distinct glycolipid at each locus is an antibody specific thereto.

10. The microarray of claim 2 wherein specifically bound to the distinct glycolipid at each spot is an antibody specific thereto.

11. The microarray of claim 3 wherein specifically bound to the distinct glycolipid at each locus is an antibody specific thereto.

12. The microarray of claim 4 wherein specifically bound to the distinct glycolipid at each spot is an antibody specific thereto.

13. The microarray of claim 1 wherein the microarray is air dried.

14. The microarray of claim 2 wherein the microarray is air dried.

15. The microarray of claim 3 wherein the microarray is air dried.

16. The microarray of claim 4 wherein the microarray is air dried.

17. A method for making a microarray of claim 1 comprising steps of printing the loci on the surface and air-drying the microarray.

18. A method for making a microarray of claim 2 comprising steps of printing the spots on the surface and air-drying the microarray.

19. A method for making a microarray of claim 3 comprising steps of printing the loci on the surface and air-drying the microarray.

20. A method for making a microarray of claim 4 comprising steps of printing the spots on the surface and air-drying the microarray.

21. A method for using a microarray of claim 1 comprising the steps of incubating the loci with the antibodies under conditions wherein each antibody binds its corresponding antigen, then washing and staining the antibody-bound loci for detection.

22. A method for using a microarray of claim 2 comprising the steps of incubating the spots with the antibodies under conditions wherein each antibody binds its corresponding antigen, then washing and staining the antibody-bound spots for detection.

23. A method for using a microarray of claim 3 comprising the steps of incubating the loci with the antibodies under conditions wherein each antibody binds its corresponding antigen, then washing and staining the antibody-bound loci for detection.

24. A method for using a microarray of claim 4 comprising the steps of incubating the spots with the antibodies under conditions wherein each antibody binds its corresponding antigen, then washing and staining the antibody-bound spots for detection.

* * * * *